US012773548B2

(12) United States Patent
Xie et al.

(10) Patent No.: US 12,773,548 B2
(45) Date of Patent: Oct. 27, 2026

(54) VENTRICULAR CONNECTING ASSEMBLY AND VENTRICULAR ASSIST SYSTEM

(71) Applicant: SHENZHEN CORE MEDICAL TECHNOLOGY CO., LTD., Shenzhen (CN)

(72) Inventors: Duanqing Xie, Shenzhen (CN); Shunzhou Yu, Shenzhen (CN)

(73) Assignee: SHENZHEN CORE MEDICAL TECHNOLOGY CO., LTD., Shenzhen (CN)

( * ) Notice: Subject to any disclaimer, the term of this patent is extended or adjusted under 35 U.S.C. 154(b) by 510 days.

(21) Appl. No.: 18/548,323

(22) PCT Filed: Jul. 26, 2022

(86) PCT No.: PCT/CN2022/107971
§ 371 (c)(1),
(2) Date: Aug. 29, 2023

(87) PCT Pub. No.: WO2023/029818
PCT Pub. Date: Mar. 9, 2023

(65) Prior Publication Data

US 2024/0131322 A1 Apr. 25, 2024
US 2024/0226534 A9 Jul. 11, 2024

(30) Foreign Application Priority Data

Sep. 6, 2021 (CN) ......................... 202111037283.3

(51) Int. Cl.
*A61M 60/861* (2021.01)
*A61M 60/178* (2021.01)
*A61M 60/216* (2021.01)

(52) U.S. Cl.
CPC ........ *A61M 60/861* (2021.01); *A61M 60/178* (2021.01); *A61M 60/216* (2021.01)

(58) Field of Classification Search
CPC .............. A61M 60/178; A61M 60/216; A61M 60/861; A61M 60/863
See application file for complete search history.

(56) References Cited

U.S. PATENT DOCUMENTS

2011/0118833 A1 5/2011 Reichenbach et al.
2013/0178694 A1 7/2013 Jeffery et al.
(Continued)

FOREIGN PATENT DOCUMENTS

CN 202338699 U 7/2012
CN 106794294 A 5/2017
(Continued)

OTHER PUBLICATIONS

Extended European Search Report issued for European Patent Application No. 22862959.8, dated Feb. 4, 2025, 6 pages.
(Continued)

*Primary Examiner* — Jon Eric C Morales
(74) *Attorney, Agent, or Firm* — HSML P.C.

(57) ABSTRACT

A ventricular connecting assembly and a ventricular assist system. The ventricular connecting assembly comprises a clamping assembly and a locking assembly; the clamping assembly comprises an opening ring, a first connecting arm and a second connecting arm, and the opening ring has a first end and a second end; the first connecting arm) and the second connecting arm are respectively connected to the first end and the second end. The locking assembly comprises a connecting member and a locking member, the connecting member is connected to the second connecting arm, and the locking member is connected to the connecting member; the locking member is rotatably abutted against the first connecting arm, the locking member can adjust the inner diameter of the opening ring during rotation, and the locking
(Continued)

member is snap-fitted with the second connecting arm to maintain the opening ring in a clamping state.

15 Claims, 6 Drawing Sheets

(56) References Cited

U.S. PATENT DOCUMENTS

| | | | |
|---|---|---|---|
| 2015/0273124 | A1 | 10/2015 | Callaway et al. |
| 2021/0001166 | A1 | 1/2021 | Stilson |

FOREIGN PATENT DOCUMENTS

| | | | | |
|---|---|---|---|---|
| CN | 107961407 | A | 4/2018 | |
| CN | 108463258 | A | 8/2018 | |
| CN | 108742735 | A | 11/2018 | |
| CN | 208764507 | U | 4/2019 | |
| CN | 109990149 | A | 7/2019 | |
| CN | 211834545 | U | * 11/2020 | ............ A61M 6/863 |
| CN | 211835566 | U | 11/2020 | |
| CN | 213139118 | U | 5/2021 | |
| CN | 113908428 | A | 1/2022 | |
| EP | 2213192 | A2 | 8/2010 | |
| JP | 2009518141 | A | 5/2009 | |
| JP | 2017518143 | A | 7/2017 | |
| WO | 2014149892 | A1 | 9/2014 | |
| WO | 2015134944 | A1 | 9/2015 | |

OTHER PUBLICATIONS

International Search Report issued for International Patent Application No. PCT/CN2022/107971, Date of mailing: Oct. 17, 2022, 7 pages including English translation.
Written Opinion issued for International Patent Application No. PCT/CN2022/107971, Date of mailing: Sep. 29, 2022, 7 pages including partial English machine translation.
Office Action issued for Chinese Patent Application No. 2021110372833, dated Mar. 31, 2022, 13 pages.
Supplementary Search Report issued for Chinese Patent Application No. 2021110372833, dated May 23, 2022, 2 pages.
Decision to Grant a Patent issued for Japanese Patent Application No. 2023-550691, Dispatch date: Jul. 2, 2024, 5 pages including English machine translation.

* cited by examiner

VENTRICULAR CONNECTING ASSEMBLY AND VENTRICULAR ASSIST SYSTEM

CROSS-REFERENCE TO RELATED APPLICATIONS

This application is an U.S. national phase application under 35 U.S.C. § 371 based upon international patent application No. PCT/CN2022/107971 filed on Jul. 26, 2022, which itself claims priority of Chinese Patent Application No, 2021/11037283.3, filed on Sep. 6, 2021, the contents of the above identified applications are hereby incorporated herein in their entireties by reference.

TECHNICAL HELD

The present disclosure relates to the technical field of medical devices, in particular to a ventricular connecting assembly and a ventricular assist system.

BACKGROUND

In blood pump implantation operations, it is usually necessary to use a ventricular connecting assembly to fix a blood pump on a biological tissue. However, the current ventricular connecting assembly is cumbersome to operate, which will bring a lot of inconvenience to the mounting of the blood pump during use.

SUMMARY

Technical Problem

The present disclosure provides a ventricular connecting assembly and a ventricular assist system to solve the problem that the operation of the ventricular connecting assembly is cumbersome and brings a lot of inconvenience to the mounting of the blood pump during use.

Technical Solution

In a first aspect, the present disclosure provides a ventricular connecting assembly, including:

a clamping assembly including a split ring, a first connecting arm, and a second connecting arm, the split ring including a first end and a second end spaced apart from the first end, an inner diameter of the split ring being adjustable, so that the split ring has a clamping state and a non-clamping state, and the first connecting arm and the second connecting arm being connected to the first end and the second end of the split ring, respectively; and a locking assembly including a connecting member and a locking member, the connecting member being connected to the second connecting arm, the locking member being rotatably connected to the connecting member, the locking member being capable of rotatably abutting against the first connecting arm, wherein the locking member is capable of adjusting relative positions of the first connecting arm and the second connecting arm when the locking member rotates, so as to adjust the inner diameter of the split ring, and the locking member is engaged with the second connecting arm to maintain the split ring in the clamped state.

In a second aspect, the present disclosure further provides a ventricular assist system, including a blood pump including an inlet tube; and the above-mentioned ventricular connecting assembly, wherein the inlet tube extends through the split ring, and the split ring is capable of clamping the inlet tube when the split ring is in the clamping state.

In a third aspect, the present disclosure also provides a ventricular assist system, including a blood pump and a ventricular connecting assembly. The blood pump includes an inlet tube, the ventricular connecting assembly includes:

a sewing ring;

a clamping assembly including a split ring, a first connecting arm, and a second connecting arm, the split ring including a first end and a second end spaced apart from the first end, an inner diameter of the split ring being adjustable, so that the split ring has a clamping state and a non-clamping state, and the first connecting arm and the second connecting arm being connected to the first end and the second end of the split ring, respectively, the annular disk being annular with an opening, and the annular disc being connected with the sewing ring, wherein the split ring is provided in an inner ring of the annular disk, a position of the opening of the split ring corresponds to a position of the opening of the annular disk, an outer ring surface of the split ring adjacent to the second end is fixedly connected to the inner ring surface of the annular disk, and an outer ring surface of the split ring adjacent to the first end is separated from the annular disk;

a locking assembly including a connecting member and a locking member, the connecting member being connected to the second connecting arm, the locking member being rotatably connected to the connecting member, and the locking member being capable of rotatably abutting against the first connecting arm, wherein the locking member is capable of adjusting relative positions of the first connecting arm and the second connecting arm when the locking member rotates, so as to adjust the inner diameter of the split ring, and the locking member is engaged with the second connecting arm to maintain the split ring in the clamped state;

wherein the inlet tube extends through the split ring, and the split ring is capable of clamping the inlet tube when the split ring is in the clamping state.

BRIEF DESCRIPTION OF THE DRAWINGS

In order to illustrate the embodiments of the present disclosure more clearly, the drawings used in the embodiments will be described briefly. Apparently, the following described drawings are merely for the embodiments of the present disclose disclosure, and other drawings can be derived by those of ordinary skill in the art without any creative effort.

DETAILED DESCRIPTION OF TILE EMBODIMENTS

The present disclosure will now be described in detail with reference to the accompanying drawings and embodiments in order to make the objects, technical solutions, and advantages of the present disclosure clearer. It should be understood that the specific embodiments described herein are only for explaining the present disclosure, and not intended to limit the present disclosure.

It should be noted that when an element is called "fixed to" or "provided on" another element, it can be directly on another element or there can be a centered element. When an element is considered to be "connected" to another element, it can be directly connected to another element or indirectly connected to the other element.

In addition, the terms "first" and "second" are only used for descriptive purposes, and should not be construed as indicating or implying relative importance or implying the number of indicated technical features. Thus, a feature delimited with "first", "second" may expressly or implicitly include at least one of the features. In the description of the present disclosure, "plurality" means two or more, unless otherwise expressly and specifically defined.

In order to illustrate the technical solution of the present disclosure, the specific drawings and embodiments will be combined to illustrate below.

Figure 1:
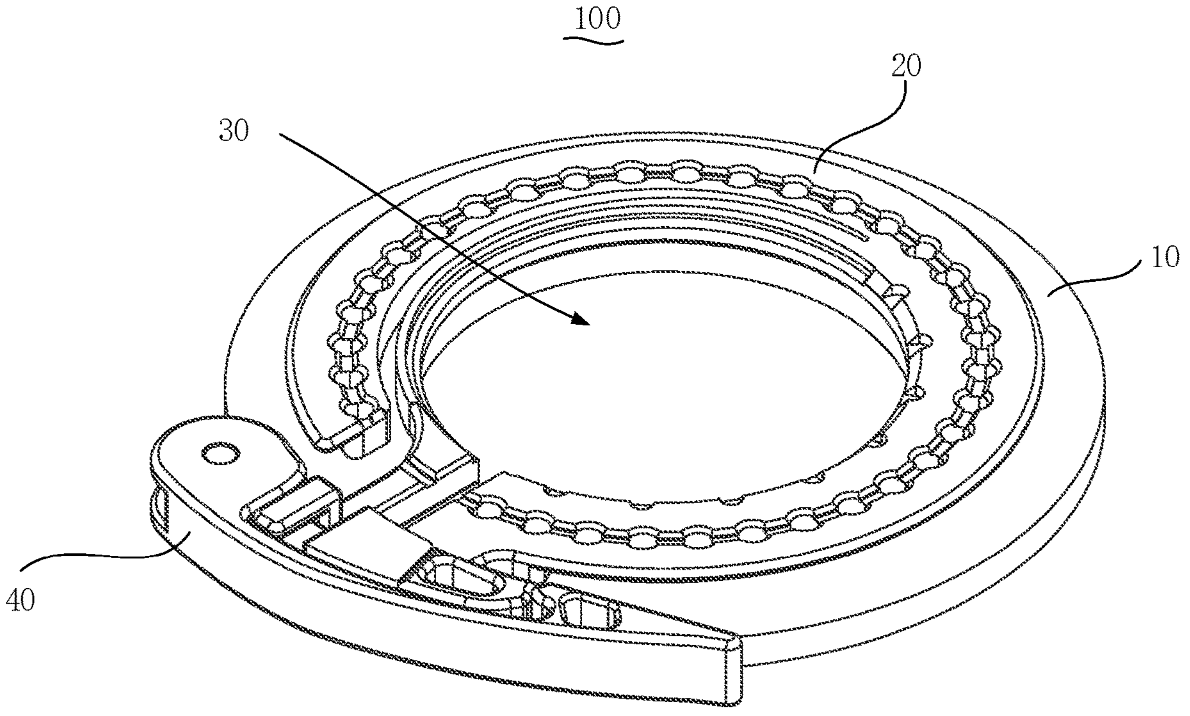
FIG. 1 is a schematic view of a ventricular connecting assembly according to an embodiment of the present disclosure.

As shown in FIG. 1, an embodiment of a first aspect of the present disclosure provides a ventricular connecting assembly 100, which especially relates to a ventricular connecting assembly 100 capable of connecting a blood pump to a biological tissue (e.g., heart tissue). The ventricular connecting assembly 100 includes a sewing ring 10, a clamping assembly 20, and a locking assembly 40.

The sewing ring 10 is configured to be secured to the biological tissue. The sewing ring 10 is of an annular structure. In some embodiments, the sewing ring 10 is sutured to the biological tissue by sutures. In some embodiments, the sewing ring 10 includes an annular cushion and a fabric layer wrapping the annular cushion. For example, the annular cushion is made of implantable silicone, and the fabric layer is made of polyester cloth.

Figure 2:
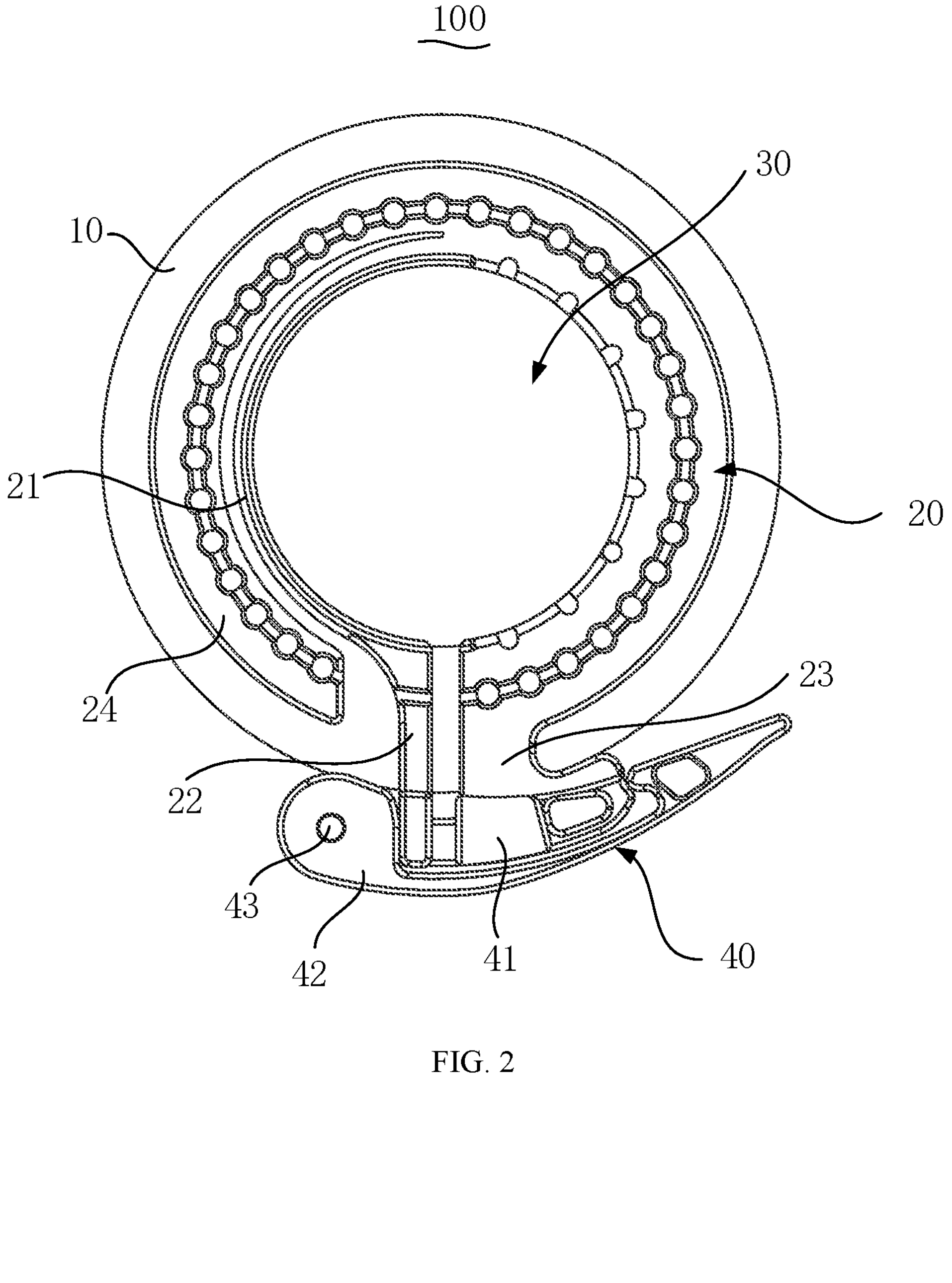
FIG. 2 is a schematic view of the ventricular connecting assembly shown in FIG. 1 viewed from another aspect.

The clamping assembly 20 is connected to the sewing ring 10. In some embodiments, the clamping assembly 20 is fixedly connected to the sewing ring 10 by sutures. In other embodiments, the clamping assembly 20 may also be connected to the sewing ring 10 by adhesives, etc. The clamping assembly 20 is configured to clamp the blood pump (e.g., an inlet tube of the blood pump). The clamping assembly 20 is provided with a clamping opening 30, the inlet tube of the blood pump can extend through the clamping opening 30 and be clamped in clamping opening 30. Referring to FIG. 2, specifically, the clamping assembly 20 includes a split ring 21, a first connecting arm 22, a second connecting arm 23, and an annular disk 24.

Figure 3:
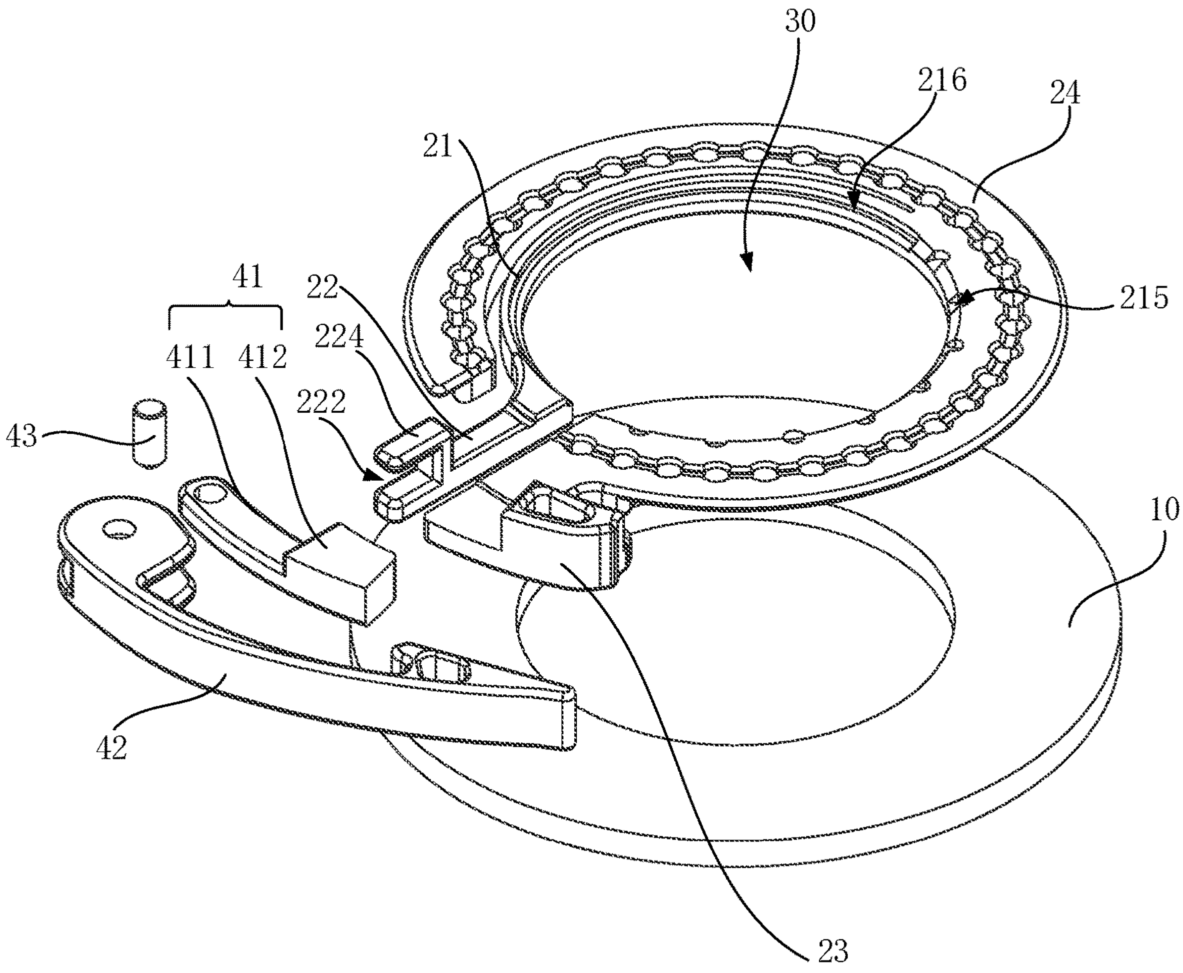
FIG. 3 is an exploded view of the ventricular connecting assembly shown in FIG. 1.
Figure 4:
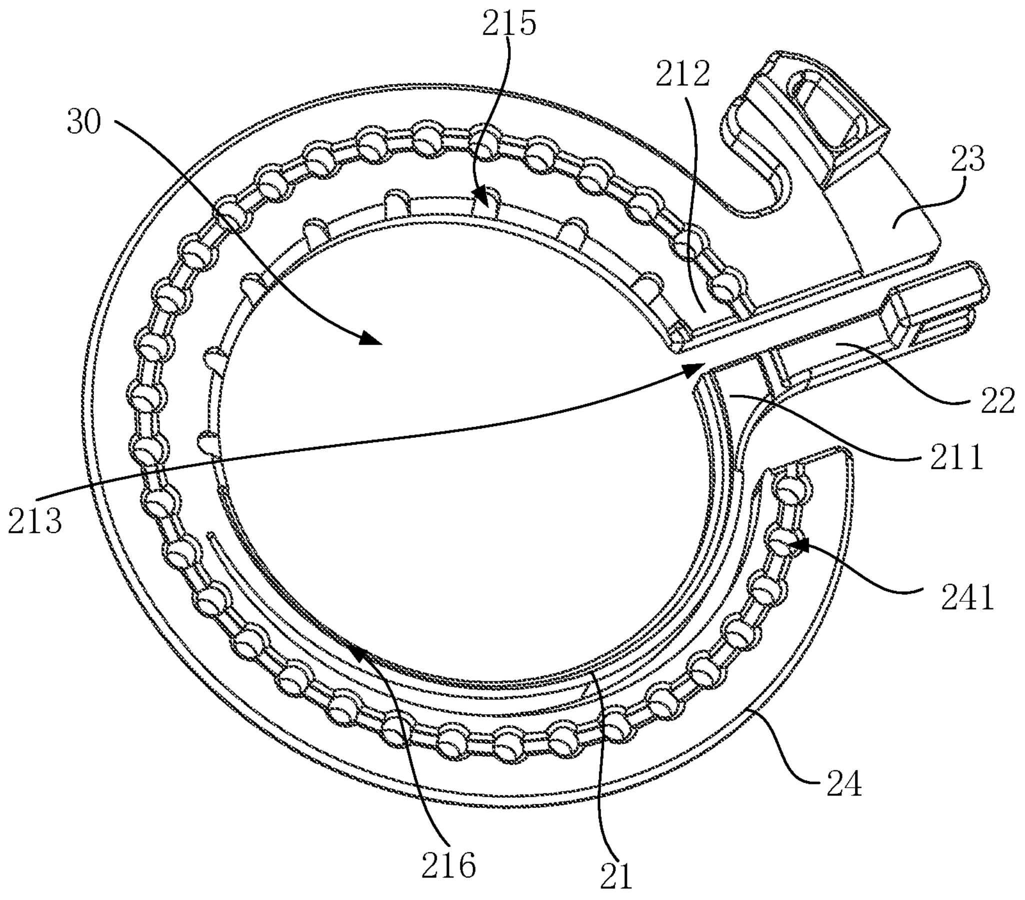
FIG. 4 is a schematic view of a clamping assembly of the ventricular connecting assembly shown in FIG. 1.

Referring to FIG. 3 and FIG. 4, the split ring 21 is configured to clamp the blood pump. The split ring 21 has a first end 211 and a second end 212 spaced apart from the first end 211. An inner diameter of the split ring 21 is adjustable, so that the split ring 21 has a clamping state and a non-clamping state. The clamping opening 30 is surrounded by the split ring 21. By adjusting the relative positions of the first end 211 and the second end 212, the inner diameter of the split ring 21 (that is, a size of the clamping opening 30) can be adjusted.

In the illustrated embodiment, the split ring 21 has a substantially annular structure with an opening 213. The first end 211 and the second end 212 of the split ring 21 are opposite and spaced apart to form the opening 213. By adjusting a distance between the first end 211 and the second end 212 (or a size of the opening 213), the inner diameter of the split ring 21 can be adjusted. When the inner diameter of the split ring 21 increases, the distance between the first end 211 and the second end 212 of the split ring 21 increases, and when the inner diameter of the split ring 21 decreases, the distance between the first end 211 and the second end 212 of the split ring 21 decreases.

The inner diameter of the split ring 21 in the clamped state is less than the inner diameter of the split ring 21 in the non-clamping state. That is, when the split ring 21 is in the clamping state, the split ring 21 has a smaller inner diameter. At this time, the split ring 21 can clamp the inlet tube of the blood pump. When the split ring 21 is in the non-clamping state, the split ring 21 has a larger inner diameter, the split ring 21 cannot clamp the inlet tube of the blood pump. At this time, the split ring 21 can loosen the inlet tube, or allow the inlet tube of the blood pump to extend through.

The first connecting arm 22 and the second connecting arm 23 are connected to the first end 211 and the second end 212 of the split ring 21, respectively. When the inner diameter of the split ring 21 increases, a distance between the first connecting arm 22 and the second connecting arm 23 increases. When the inner diameter of the split ring 21 decreases, the distance between the first connecting arm 22 and the second connecting arm 23 decreases. Specifically, the first connecting arm 22 and the second connecting arm 23 are bent and extended from the first end 211 and the second end 212 of the split ring 21, respectively, in a direction away from the split ring 21.

In one of the embodiments, in the non-clamping state (or in an initial state), a side of the first connecting arm 22 facing the second connecting arm 23 is parallel to a side of the second connecting arm 23 facing the first connecting arm 22. In other embodiments, in the non-clamping state (or in the initial state), from an end adjacent to the split ring 21 to an end away from the split ring 21, a distance between the side of the first connecting arm 22 facing the second connecting arm 23 and the side of the second connecting arm 23 facing the first connecting arm 22 gradually increases. It should be understood that, in other embodiments, in the non-clamping state, from the end adjacent to the split ring 21 to the end away from the split ring 21, a distance between the side of the first connecting arm 22 facing the second connecting arm 23 and the side of the second connecting arm 23 facing the first connecting arm 22 gradually decreases.

In some embodiments, the first connecting arm 22 and the first end 211 of the split ring 21 may be integrally formed. Alternatively, the independent first connecting arm 22 is connected to the first end 211 of the split ring 21 by, such as welding, etc. The second connecting arm 23 may be integrally formed with the second end 212 of the split ring 21. Alternatively, the independent second connecting arm 23 is be connected to the second end 212 of the split ring 21 by, such as welding, etc.

The annular disk 24 is fixedly connected to the sewing ring 10. In one embodiment, the annular disk 24 is fixedly connected to the sewing ring 10 by sutures. In the embodiment, the annular disk 24 is provided with a suture hole 241, and the sewing ring 10 and the annular disk 24 are fixedly connected by sutures extending through the sewing ring 10 and the suture hole 241. It should be understood that, in other embodiments, the annular disk 24 may also be connected to the sewing ring 10 by adhesive, etc.

Figure 5:
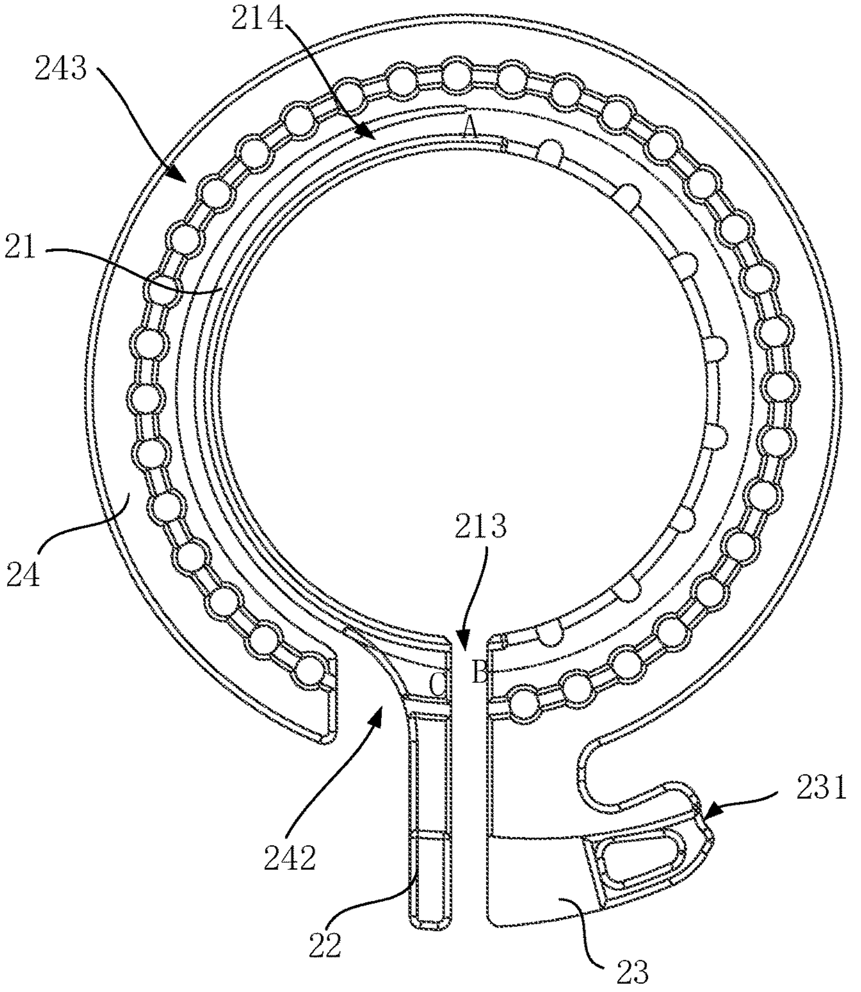
FIG. 5 is a schematic view of the clamping assembly shown in FIG. 4 viewed from another aspect.

Referring to FIG. 5, the annular disk 24 has an annular structure with an opening 242. The split ring 21 is provided in an inner ring of the annular disk 24, a position of the opening 213 of the split ring corresponds to a position of the opening 242 of the annular disk 24. An outer ring surface of the split ring 21 adjacent to the second end 212 (i.e., a portion of the outer ring surface corresponding to the arc AB shown in the figure) is fixedly connected to the inner ring surface of the annular disk 24, and an outer ring surface of the split ring 21 adjacent to the first end 211 (i.e., a portion of the outer ring surface corresponding to the arc AC shown in the figure) is separated from the annular disk 21. That is, a part of the outer ring surface of the split ring 21 is fixedly connected to the inner ring surface of the annular disk 24, and another part of the outer ring surface of the split ring 21 is separated from the inner ring surface of the annular disk 24. The above-mentioned method can not only ensure the reliable connection between the split ring 21 and the annular disk 24, but also ensure that the split ring 21 has a certain degree of elasticity, which facilitates the adjustment of the inner diameter of the split ring 21.

In one of the embodiments, a length of the portion of the outer ring surface of the split ring 21 fixedly connected to the inner ring face of the annular disk 24 (approximately a length of the arc AB shown in the figure) is less than or equal to half of a length of the outer ring face of the split ring 21 (approximately a length of the arc BC shown in the figure). That is, along a circumferential direction of the split ring 21, the length of the portion of the outer ring surface of the split ring 21 fixedly connected to the inner ring face of the annular disk 24 is less than or equal to half of the length of the outer ring face of the split ring 21. By adopting the above solution, a high connection strength between the split ring and the annular disk 24 can be ensured, while ensuring the split ring 21 has a certain degree of elasticity.

It should be understood that, in other embodiments, the length of the portion of the outer ring surface of the split ring 21 fixedly connected to the inner ring face of the annular disk 24 may also be greater than half of the length of the outer ring face of the split ring 21.

In one of the embodiments, a position of a junction of separation and connection between the outer ring surface of the split ring 21 and the inner ring face of the annular disk 24 (approximately a position of point A shown in the figure) is opposite to a position of the opening 213 of the split ring 21.

The split ring 21 is coplanar with a side of the annular disk 24 away from the sewing ring 10. That is, a surface 214 of the split ring 21 away from the sewing ring 10 is coplanar with a surface 243 of the annular disk 24 away from the sewing ring 10, thereby reducing a thickness of the clamping assembly 20 and simplifying the structure. Specifically, a surface of the split ring 21 facing the sewing ring 10 is coplanar with a surface of the annular disk 24 facing the sewing ring 10.

Figure 6:
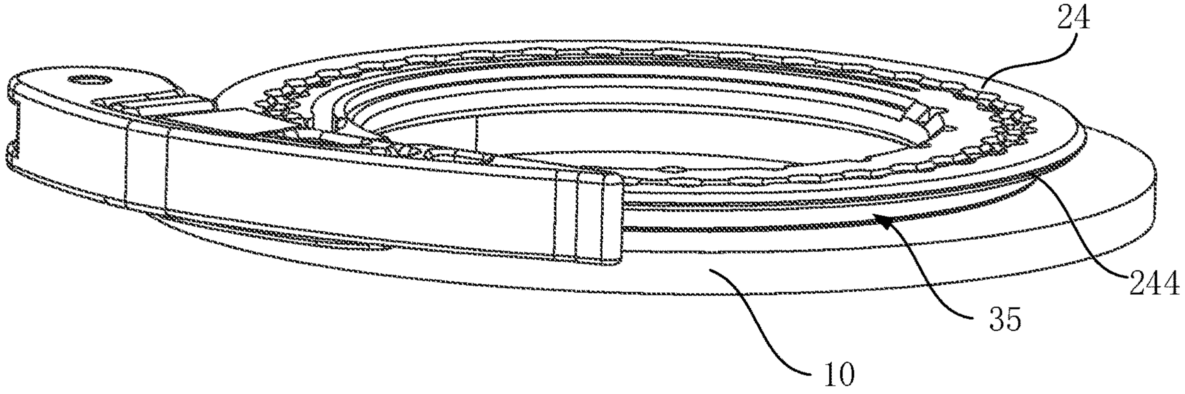
FIG. 6 is a schematic view of the ventricular connecting assembly shown in FIG. viewed from another aspect.

Referring to FIG. 6, in some embodiments, a flange 244 is provided on an outer periphery of a side of the annular disk 24 away from the sewing ring 10, so that a recessed limiting area 35 can be formed between the sewing ring 10 and the flange 244 for a surgical clamp to clamp the ventricular connecting assembly 100, which is convenient for an operator to clamp the ventricular connecting assembly 100 with the surgical clamp during the operation.

In one of the embodiments, the split ring 21 and the annular disk 24 are integrally formed. For example, an end of an open annular plate may be provided with a slot extending along a circumferential direction, and the slot extends from an end of the annular plate to a middle of the annular plate in the circumferential direction, so that the split ring 21 and annular disk 24 are integrally formed, or, may be obtained by metal injection molding, metal casting molding and other methods. In some embodiments, the split ring 21, the first connecting arm 22, the second connecting arm 23, and the annular disk 24 are integrally formed, that is, the entire clamping assembly 20 is integrally formed. At this time, the integrally formed clamping assembly 20 can still be manufactured by the above method.

Referring to FIG. 2 and FIG. 3 again, the locking assembly 40 can adjust the inner diameter of the split ring 21 and maintain the split ring 21 in the clamping state. The locking assembly 40 includes a connecting member 41 and a locking member 42. The connecting member 41 is connected to the second connecting arm 23, and the locking member 42 is rotatably connected to the connecting member 41. In an embodiment, an independent rotating shaft 43 may be provided, which can be movably extend through the locking member 42 and the connecting member 41. Alternatively, the rotating shaft 43 is fixedly connected to the locking member 42, and the connecting member 41 is rotatably connected to the rotating shaft 43. Alternatively, the rotating shaft 43 is rotatably connected to the locking member 42 and fixedly connected to the connecting member 41.

The locking member 42 can rotatably abut against the first connecting arm 22. When the locking member 42 rotates, it can adjust relative positions of the first connecting arm 22 and the second connecting arm 23, so as to adjust the inner diameter of the split ring 21, and the switching of the split ring 21 between the clamping state and the non-clamping state can be achieved.

The locking member 42 is engaged with the second connecting arm 23 to maintain the relative positions of the first connecting arm 22 and the second connecting arm 23, and to keep the distance between the first connecting arm 22 and the second connecting arm 23 unchanged, so as to maintain the split ring 21 in the clamping state, so that the inlet tube of the blood pump is clamped and fixed. By rotating the locking member 42 relative to the first connecting arm 23, the locking member 42 can be engaged with and disengaged from the second connecting arm 23.

In the ventricular connecting assembly 100 according to the embodiment of the present disclosure, the relative positions of the first connecting arm 22 and the second connecting arm 23 are adjusted by rotating the locking member 42, so as to adjust the inner diameter of the split ring 21, so that the split ring 21 can be switched between the clamping state and the non-clamping state to realize the locking and loosening of the inlet tube of the blood pump, and the operation is simple and convenient. By engaging the locking member 42 with the second connecting arm 23, the relative positions of the first connecting arm 22 and the second connecting arm 23 can be maintained, and the split ring 21 is maintained in the clamping state, so that the inlet tube of the blood pump is clamped and fixed without using sutures or fasteners to maintain the split ring 21 in the clamping state, so that the mounting of the blood pump is also relatively simple.

In one of the embodiments, the first connecting arm 22 is a movable arm, and the second connecting arm 23 is a fixed arras. When the locking member 42 rotates, the first connecting arm 22 can move toward or away from the second connecting arm 23. In some other embodiments, both the first connecting arm 22 and the second connecting arm 23 are movable arms, and when the locking member 42 rotates, the first connecting arm 22 and the second connecting arm 23 can move toward or away from each other. Alternatively, the first connecting arm 22 is a fixed arm, the second connecting arm 23 is a movable arm, and when the locking member 42 rotates, the second connecting arm 23 can move toward or away from the first connecting arm 22.

In some embodiments, in order to facilitate the rotation of the locking member 42 to adjust the relative positions of the first connecting arm 22 and the second connecting arm 23, the relative positions of the first connecting arm 22 and the second connecting arm 23 are maintained by engaging the locking member 42 with the second connecting arm 23. The locking member 42 is capable of rotatably abutting against the side of the first connecting arm 22 away from the second connecting arm 23. When the locking member 42 is engaged with the second connecting arm 23, a portion of the locking member 42 that engages with the second connecting arm 23 exerts a force or force component in a direction toward the first connecting arm 23 on the second connecting arm 23. That is, when the locking member 42 is engaged with the second connecting arm 23, the locking member 42 applies a first force or a first component force to the first connecting arm 22 in a direction toward the second connecting arm 22, and a portion of the locking member 42 engaged with the second connecting arm 23 exerts a second force or a second force component to the second connecting arm 23 in a direction toward the first connecting arm 22. Under the action of the first force or the first component force, the second force or the second component force, the relative positions of the first connecting arm 22 and the second connecting arm 23 will be maintained. Thus, the way of engaging the locking member 42 with the second connecting arm 23 may be, for example, that the locking member 42 is engaged with the side of the second connecting arm 23 away from the first connecting arm 22. Alternatively, a cooperating portion is provided on the second connecting arm 23 that cooperates with the locking member 42. The cooperating portion may be a groove whose opening is away from the first connecting arm 22, a surface away from the first connecting arm 22, or a protrusion extending away from the first connecting arm 22.

Figure 7:
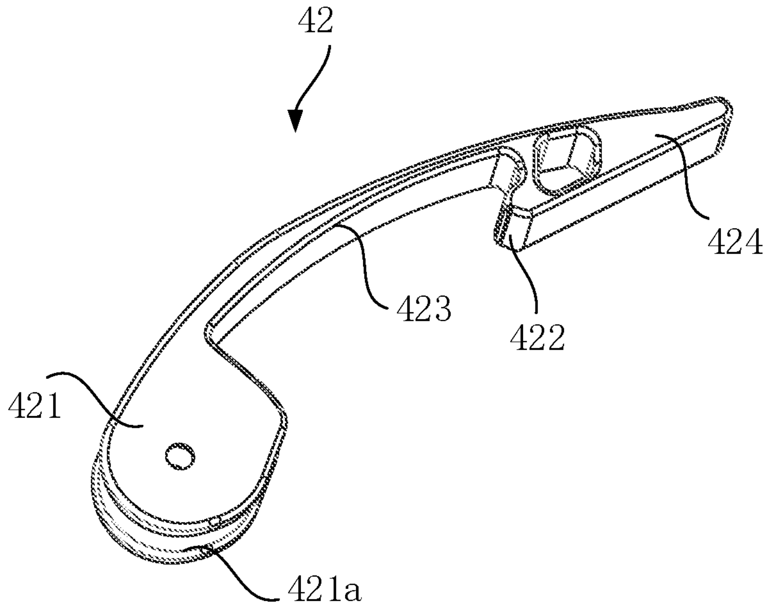
FIG. 7 is a schematic view of a locking member of the ventricular connecting assembly shown in FIG. 2.
Figure 8:
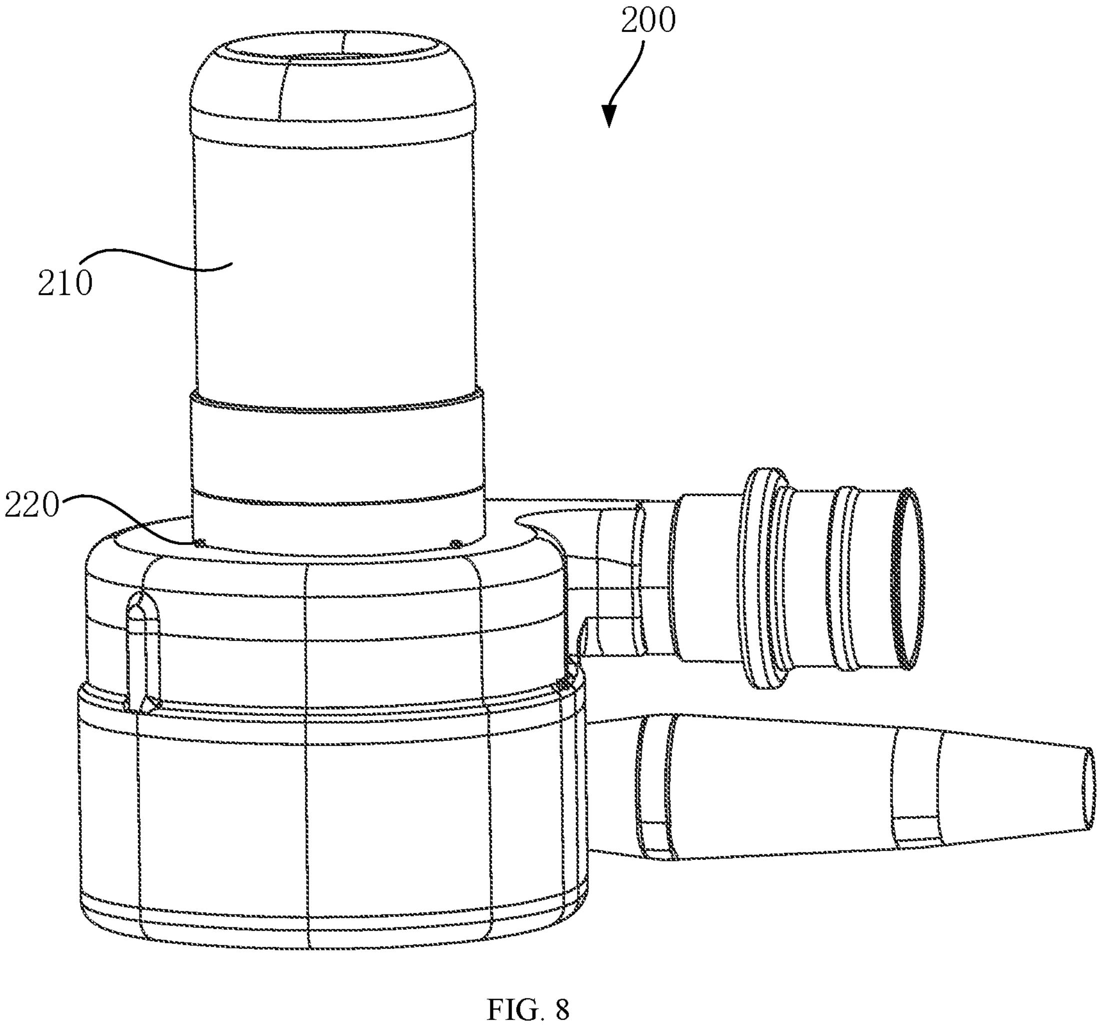
FIG. 8 is a schematic view of a blood pump according to the present disclosure.

Referring to FIG. 7, in an embodiment, the locking member 42 includes a cam end 421, and the cam end 421 abuts against the side of the first connecting arm 22 away from the second connecting arm 23. The cam end 421 can rotate relative to the first connecting arm 22, so as to adjust the relative positions of the first connecting arm 22 and the second connecting arm 23. During the rotation relative to the first connecting arm 22, the cam end 421 can push the first connecting arm 22 away from or adjacent to the second connecting arm 23, so that the relative positions of the first connecting arm 22 and the second connecting arm 23 are adjusted, and the inner diameter of the split ring 21 is further adjusted, therefore the split ring 21 can be switched between the clamping state and the non-clamping state.

By adopting the above solution, the distance between the first connecting arm 22 and the second connecting arm 23 is adjusted by the rotation of the cam end 421 relative to the first connecting arm 22, which not only can simplify the operation, but also can strengthen the snapping stability between the locking member 42 and the second connecting arm 23, further ensuring that the risk of loosening between the locked locking member 42 and the second connecting arm 23 is reduced.

Referring to FIG. 5 and FIG. 7, in some embodiments, the side of the second connecting arm 23 away from the first connecting atm 22 is provided with an engaging portion 231, and the locking member 42 is provided with a cooperation portion 422 cooperating with the engaging portion 231. The cooperation portion 422 can be engaged with and disengaged from the engaging portion 231 by rotating the locking member 42 relative to the first connecting arm. Specifically, the engaging portion 231 is a groove, and the cooperation portion 422 is a protrusion, or the engaging portion 231 is a protrusion, and the cooperation portion 422 is a groove.

In the illustrated embodiment, the locking member 42 further includes a connecting portion 423 having an end fixedly connected to the cam end 421, and a handle portion 424 fixedly connected to an end of the connecting portion 423 away from the cam end 421, and the cooperation portion 422 is provided on the handle portion 424. The cam end 421 is arranged opposite to the cooperation portion 422. Specifically, the connecting portion 423 is shaped substantially as an arc strip.

By adopting the above solution, the locking member 42 can be quickly engaged with the second connecting arm 23, and the locking member 42 can be stably engaged with the second connecting arm 23, so that the inlet tube of the blood pump can be clamped and fixed. The structure is simple and the operation is quick.

In some embodiments, the first connecting arm 22 is provided with a guiding groove 222. One end of the connecting member 41 is fixedly connected to the second connecting arm 23, the other end of the connecting member 41 is rotatably connected to the locking member 42, and a middle portion of the connecting member 41 slidably extends through the guiding groove 222. Such configuration can limit the position of the connecting member 41 and prevent the connecting member 41 from being deflected, thereby preventing the connecting member 41 from being deflected when the locking member 42 rotates relative to the second connecting arm 23, and further ensuring that the first connecting arm 22 and the second connecting arm 23 will not be misaligned when clamping the inlet tube of the blood pump.

Referring to FIG. 3 again, in some embodiments, the connecting member 41 includes a rod portion 411 and a limiting block 412 provided at an end of the rod portion 411. An end of the rod portion 411 away from the limiting block 412 is rotatably connected to the locking member 42, and the limiting block 412 is capable of abutting against the side of the second connecting arm 23 adjacent to the first connecting arm 22, so as to prevent the first connecting arm 22 from continuously moving in a direction toward the second connecting arm 23, and keep the relative positions of the first connecting arm 22 and the second connecting arm 23. The risk of the locking member 42 coming loose from the second connecting arm 23 is reduced. Specifically, the rod portion 411 of the connecting member 41 slidably extends through the guiding groove 222.

Referring to FIG. 7 again, in the illustrated embodiment, the cam end 421 of the locking member 42 is provided with two spaced cam portions 421*a*. The end of the first connecting arm 22 away from the split ring 21 is formed with a U-shaped portion 224, the shaped portion 224 surrounds the guiding groove 222. The two cam portions 421*a* are capable of rotatably abutting against two arms of the U-shaped portion 224, respectively. The rotating shaft 43 extends through the connecting member 41, and two ends of the rotating shaft 43 are connected to the two cam portions 421*a*, respectively. The two cam portions 421*a* are parallel.

Referring to FIG. 1, FIG. 3, FIG. 4, and FIG. 8, the embodiment of a second aspect of the present disclosure provides a ventricular assist system, which includes a blood pump 200 and the above-mentioned ventricular connecting assembly 100.

The blood pump 200 includes an inlet tube 210. The inlet tube 210 extends through the split ring 21, and the split ring 21 is capable of clamping the inlet tube 210 when the split ring 21 is in a clamping state.

In the ventricular assist system of the present disclosure, since the locking member 42 is capable of adjusting the relative positions of the first connecting arm 22 and the second connecting arm 23 when rotating, the inner diameter of the split ring 21 can be adjusted, so that the split ring 21 can be switched between the clamping state and the non-clamping state, the inlet tube 210 of the blood pump 200 can be clamped or loosened, the structure is simple, the operation is convenient, and the mourning of the blood pump 200 is convenient.

In some embodiments, an inner ring wall of the split ring 21 is provided with a positioning groove 215, an outer peripheral surface of the inlet tube 210 is provided with a positioning protrusion 220, and the positioning protrusion 220 is capable of being accommodated in the positioning groove 215 to prevent the inlet tube 210 and the split ring 21 from rotating relative to each other.

By adopting the above solution, when the inlet tube 210 is clamped and fixed by the ventricular connecting assembly 100, the relative rotation between the inlet tube 210 and the ventricular connecting assembly 100 can be avoided.

In some embodiments, a plurality of positioning protrusions 220 are provided, which can improve the ability of the positioning protrusions 220 to limit the relative rotation between the inlet tube 210 and the split ring 21. The plurality of positioning protrusions 220 surround the inlet tube 210 to limit the relative rotation of the inlet tube 210 and the split ring 21 at a plurality of positions, thereby improving the stability thereof.

In the embodiment, the positioning groove 214 is provided on the inner ring wall of the portion of the split ring 21 fixedly connected to the ring disk 24, and the inner ring wall of the portion of the split ring 21 that is separated from the ring disk 24 is further provided with an avoidance groove 216 extending in the circumferential direction of the split ring 21. Part of the positioning protrusions 220 are capable of being accommodated in the positioning groove 215 to limit the relative rotation of the inlet tube 210 and the split ring 21, and the rest part of positioning protrusions 220 are capable of being accommodated in the avoidance groove 216 to prevent the remaining positioning protrusions 220 from interfering with the inner ring wall of the split ring 21.

It should be noted that the ventricular connecting assembly is not limited to the above structure. In some embodiments, the sewing ring 10 can also be omitted, and the clamping assembly 40 can be directly sutured on the biological tissue.

The clamping assembly 20 is not limited to the above-mentioned structure. In some embodiments, the split ring 21 is not arranged in the inner ring of the annular disk 24, and the split ring 21 and the annular disk 24 are arranged coaxially. At this time, the annular disk 24 may be a complete ring structure instead of an open annular structure, or, in some embodiments, the split ring 21 can also be partially accommodated in the inner ring of the annular disk 24, or, in other embodiments, the clamping assembly 20 does not have the annular disk 24, and a portion of the outer peripheral surface of the split ring 21 is bent and extended to form a flange configured to be fixed connected to the sewing ring 10 or biological tissue.

The foregoing descriptions are merely specific embodiments of the present disclosure, but are not intended to limit the protection scope of the present disclosure. Any variation or replacement readily figured out by a person skilled in the art within the technical scope disclosed in the present disclosure shall all fall within the protection scope of the present disclosure.

What is claimed is:

1. A ventricular connecting assembly, comprising:

a clamping assembly comprising a split ring, a first connecting arm, and a second connecting arm, the split ring comprising a first end and a second end spaced apart from the first end, an inner diameter of the split ring being adjustable, so that the split ring has a clamping state and a non-clamping state, and the first connecting arm and the second connecting arm being connected to the first end and the second end of the split ring, respectively; and a locking assembly comprising a connecting member and a locking member, the connecting member being connected to the second connecting arm, the locking member being rotatably connected to the connecting member, the locking member being capable of rotatably abutting against the first connecting arm, wherein the locking member is capable of adjusting relative positions of the first connecting arm and the second connecting arm when the locking member rotates, so as to adjust the inner diameter of the split ring, and the locking member is engaged with the second connecting arm to maintain the split ring in the clamped state, wherein the locking member comprises a cam end, the cam end is capable of rotatably abutting against a side of the first connecting arm away from the second connecting arm, and the cam end is capable of adjusting the relative positions of the first connecting arm and the second connecting arm when the cam end rotates relative to the first connecting arm, and wherein the cam end of the locking member is provided with two spaced cam portions, an end of the first connecting arm away from the split ring is formed with a U-shaped portion, and the two cam portions are capable of rotatably abutting against two arms of the U-shaped portion, respectively.

2. The ventricular connecting assembly according to claim 1, wherein the locking member further comprises a connecting portion and a handle portion, an end of the connecting portion is fixedly connected to the cam end, the handle portion is fixedly connected to an end of the connecting portion away from the cam end, a side of the second connecting arm away from the first connecting arm is provided with an engaging portion, the locking member comprises a cooperation portion cooperating with the engaging portion, and the cooperation portion is provided on the handle portion and is arranged opposite to the cam end.

3. The ventricular connecting assembly according to claim 1, wherein a side of the second connecting arm away from the first connecting arm is provided with an engaging portion, the locking member is provided with a cooperation portion cooperating with the engaging portion, and the cooperation portion is engaged with and disengaged from the engaging portion by rotating the locking member relative to the first connecting arm.

4. The ventricular connecting assembly according to claim 3, wherein one of the engaging portion and the cooperation portion is a groove, and the other one of the engaging portion and the cooperation portion is a protrusion.

5. The ventricular connecting assembly according to claim 1, wherein the connecting member comprises a rod portion and a limiting block provided at an end of the rod portion, an end of the rod portion away from the limiting block is rotatably connected to the locking member, and the limiting block is capable of abutting against a side of the second connecting arm adjacent to the first connecting arm.

6. A ventricular connecting assembly, comprising:

a clamping assembly comprising a split ring, a first connecting arm, and a second connecting arm, the split ring comprising a first end and a second end spaced apart from the first end, an inner diameter of the split ring being adjustable, so that the split ring has a clamping state and a non-clamping state, and the first connecting arm and the second connecting arm being connected to the first end and the second end of the split ring, respectively; and a locking assembly comprising a connecting member and a locking member, the connecting member being connected to the second connecting arm, the locking member being rotatably connected to the connecting member, the locking member being capable of rotatably abutting against the first connecting arm, wherein the locking member is capable of adjusting relative positions of the first connecting arm and the second connecting arm when the locking member rotates, so as to adjust the inner diameter of the split ring, and the locking member is engaged with the second connecting arm to maintain the split ring in the clamped state, wherein the first connecting arm is provided with a guiding groove, one end of the connecting member is fixedly connected to the second connecting arm, the other end of the connecting member is rotatably connected to the locking member, and a middle portion of the connecting member slidably extends through the guiding groove.

7. The ventricular connecting assembly according to claim 1, wherein the clamping assembly further comprises an annular disk having an opening, the split ring is provided in an inner ring of the annular disk, a position of an opening of the split ring corresponds to a position of the opening of the annular disk, an outer ring surface of the split ring adjacent to the second end is fixedly connected to an inner ring surface of the annular disk, and an outer ring surface of the split ring adjacent to the first end is separated from the annular disk.

8. The ventricular connecting assembly according to claim 7, wherein a length of a portion of the outer ring surface of the split ring fixedly connected to the inner ring face of the annular disk is less than or equal to half of a length of the outer ring face of the split ring.

9. The ventricular connecting assembly according to claim 7, wherein a position of a junction of separation and connection between the outer ring surface of the split ring and the inner ring face of the annular disk is opposite to a position of the opening of the split ring.

10. The ventricular connecting assembly according to claim 7, further comprising a sewing ring fixedly connected to the annular disk, the split ring being coplanar with a side of the annular disk away from the sewing ring.

11. The ventricular connecting assembly according to claim 7, further comprising a sewing ring fixedly connected to the annular disk, wherein a flange is provided on an outer periphery of a side of the annular disk away from the sewing ring.

12. The ventricular connecting assembly according to claim 7, wherein the split ring and the annular disk are integrally formed.

13. A ventricular assist system, comprising:

a blood pump comprising an inlet tube; and the ventricular connecting assembly according to claim 1, wherein the inlet tube extends through the split ring, and the split ring is capable of clamping the inlet tube when the split ring is in the clamping state.

14. The ventricular assist system according to claim 13, wherein an inner ring wall of the split ring is provided with a positioning groove, an outer peripheral surface of the inlet tube is provided with a positioning protrusion, and the positioning protrusion is capable of being accommodated in the positioning groove.

15. A ventricular assist system, comprising a blood pump and a ventricular connecting assembly, the blood pump comprising an inlet tube, the ventricular connecting assembly comprising:

a sewing ring;

a clamping assembly comprising a split ring, a first connecting arm, a second connecting arm, and an annular disk, the split ring comprising a first end and a second end spaced apart from the first end, an inner diameter of the split ring being adjustable, so that the split ring has a clamping state and a non-clamping state, and the first connecting arm and the second connecting arm being connected to the first end and the second end of the split ring, respectively, the annular disk being annular with an opening, and the annular disc being connected with the sewing ring, wherein the split ring is provided in an inner ring of the annular disk, a position of the opening of the split ring corresponds to a position of the opening of the annular disk, an outer ring surface of the split ring adjacent to the second end is fixedly connected to the inner ring surface of the annular disk, and an outer ring surface of the split ring adjacent to the first end is separated from the annular disk;

a locking assembly comprising a connecting member and a locking member, the connecting member being connected to the second connecting arm, the locking member being rotatably connected to the connecting member, and the locking member being capable of rotatably abutting against the first connecting arm, wherein the locking member is capable of adjusting relative positions of the first connecting arm and the second connecting arm when the locking member rotates, so as to adjust the inner diameter of the split ring, and the locking member is engaged with the second connecting arm to maintain the split ring in the clamped state;

wherein the inlet tube extends through the split ring, and the split ring is capable of clamping the inlet tube when the split ring is in the clamping state, wherein an inner ring wall of the split ring is provided with a positioning groove, an outer peripheral surface of the inlet tube is provided with a positioning protrusion, and the positioning protrusion is capable of being accommodated in the positioning groove, wherein a plurality of positioning protrusions are provided, and the plurality of positioning protrusions surround the inlet tube, and wherein the positioning groove is provided on the inner ring wall of a portion of the split ring fixedly connected to the ring disk, the inner ring wall of a portion of the split ring that is separated from the ring disk is further provided with an avoidance groove extending in a circumferential direction of the split ring, part of the positioning protrusions are capable of being accommodated in the positioning groove, and the rest part of positioning protrusions are capable of being accommodated in the avoidance groove.

* * * * *